United States Patent [19]

Polley

[11] 4,384,960
[45] May 24, 1983

[54] IODINE DISPENSER AND METHOD OF DISPENSING IODINE

[76] Inventor: Richard D. Polley, 9111 Park Dr., Miami Shores, Fla. 33138

[21] Appl. No.: 93,542

[22] Filed: Nov. 13, 1979

[51] Int. Cl.³ .............................................. C02F 1/76
[52] U.S. Cl. ..................................... 210/753; 210/764; 424/150
[58] Field of Search ................ 222/1, 189, 206, 215, 222/420, 543, 190, 158, 549, 562; D9/367, 403, 413, 446; 128/232, 272; 422/261, 276, 277, 294, 37; 210/753, 764, 244; 423/500; 424/150

[56] References Cited

U.S. PATENT DOCUMENTS

| | | |
|---|---|---|
| 310,130 | 12/1884 | Frank . |
| 707,873 | 8/1902 | Spencer .......................... 210/244 X |
| 1,771,519 | 7/1930 | Allen ................................... 422/261 |
| 2,073,021 | 3/1937 | McQuiston ..................... 423/500 X |
| 2,211,837 | 8/1940 | Rice et al. ........................... 424/150 |
| 2,347,567 | 4/1944 | Kresse . |
| 2,385,394 | 9/1945 | Witte .................... 424/150 |
| 2,594,093 | 4/1952 | Thompson .......................... 128/272 |
| 2,697,841 | 12/1954 | Collins . |
| 2,743,208 | 4/1956 | Marcuse et al. ..................... 424/150 |
| 2,761,833 | 9/1956 | Ward .............................. 222/189 X |
| 2,783,919 | 3/1957 | Ansell . |
| 2,819,825 | 1/1958 | Quinche et al. ..................... 222/215 |
| 2,987,223 | 6/1961 | Armour .......................... 222/420 X |
| 3,080,217 | 3/1963 | Myers ............................. 423/500 |
| 3,088,634 | 5/1963 | Rosekrans et al. ............. 222/190 X |
| 3,279,996 | 10/1966 | Long, Jr. et al. ............... 128/272 X |
| 3,282,478 | 11/1966 | Russell ........................... 222/543 X |
| 3,354,883 | 11/1967 | Southerland .................... 222/215 X |
| 3,408,295 | 10/1968 | Vaichulis ............................. 210/753 |
| 3,772,193 | 11/1973 | Nelli et al. ......................... 210/756 |
| 3,857,423 | 12/1974 | Ronca, Jr. ....................... 222/215 X |
| 3,951,798 | 4/1976 | Haldopoulos ................... 222/189 X |

FOREIGN PATENT DOCUMENTS 877707  9/1961  United Kingdom ............... 222/215

Primary Examiner—Robert B. Reeves
Assistant Examiner—Edward M. Wacyra
Attorney, Agent, or Firm—Anthony A. O'Brien

[57] ABSTRACT

An iodine dispenser for water disinfection and/or treatment purposes includes a squeezable plastic container containing elemental iodine therein. The iodine is dispensed by placing water within the container to dissolve at least a portion of the iodine and then dispensing the iodine solution from the container.

10 Claims, 8 Drawing Figures

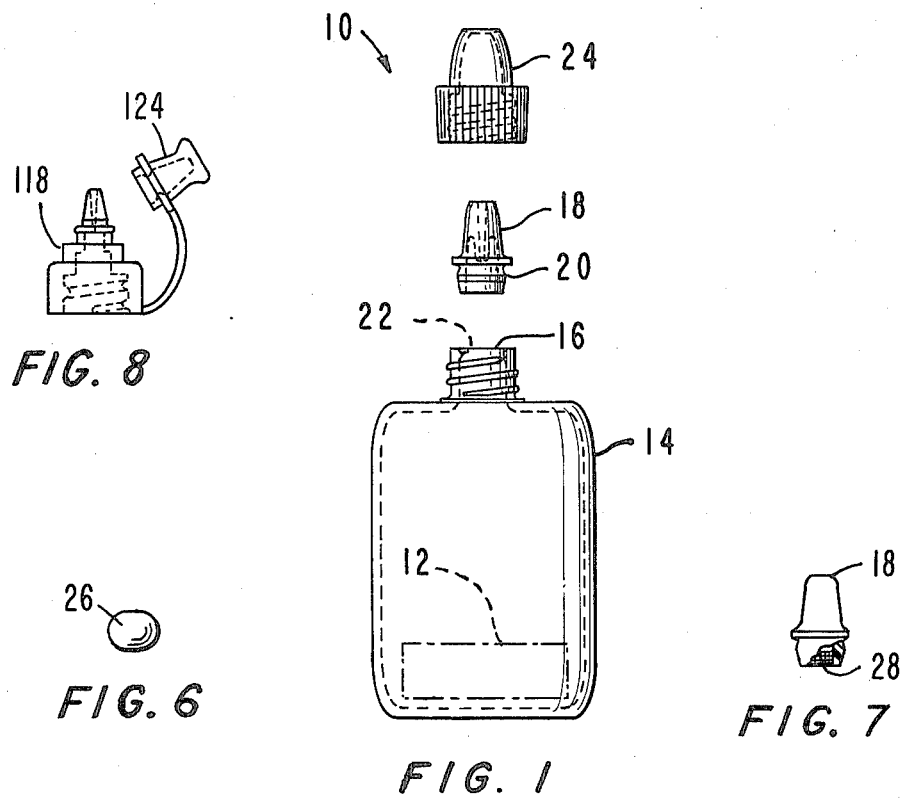

IODINE DISPENSER AND METHOD OF DISPENSING IODINE

TECHNICAL FIELD

The present invention relates to the storage and dispensing of iodine for disinfecting water, disinfecting vegetables, treating animals or human beings to cure or prevent iodine-deficient goiter, prevent accumulation of radioactive iodine in the thyroid gland from air, food and water following radiation exposure, disinfecting wounds, or the like.

DESCRIPTION OF THE PRIOR ART

Generally city water supply systems introduce chlorine or a compound of chlorine into water in the water supply system between the source of the water and the point where the water supply system branches to various scattered users in order to destroy pathogens and render the water potable. The chlorine or chlorine compound remains effective for only a relatively short period of time. In the event of a disaster such as a nuclear disaster or any other type of disaster, the water supply system can be disrupted allowing contamination with pathogenic organisms. In a nuclear disaster the water supply system can be contaminated with radioactive iodine. The air can also become contaminated with radioactive iodine, presenting another vector for medical danger to the human and livestock thyroid gland. Additionally, travellers, hunters, campers, fisherman, military personnel and others are often in areas where there is an absence of a known potable water supply; a suspect water source can be rendered potable by boiling, but this requires suitable heating and boiling facilities to render the water potable. Thus there exists a need for simple methods and/or devices which can be stockpiled for indefinite periods of time to be distributed in event of a disaster and which are inexpensive, small and easily portable so that suspect water can be readily disinfected.

The use of iodine and compounds of iodine for disinfecting or purifying water and other sanitation purposes is disclosed in the prior art, as exemplified in U.S. Pat. No. 310,130, No. 2,347,567, No. 2,743,208 and No. 3,408,295. The above patent 3,408,295 particularly discloses an apparatus and method for disinfecting or purifying water wherein the water is admitted through an inlet of the container, passed through a bed of iodine crystals and then through a porous body which prevents passage of the iodine crystals to an outlet of the container. This patent 3,408,295 states that water solutions of iodine obtained by the apparatus thereof can be employed to purify larger volumes of water. Iodine is known to have excellent germicidal properties, destroying bacteria, spores, amoebic and other protozoan cysts, viruses, and fungi, including all pathogenic forms; these germicidal properties make iodine especially suitable for water purification purposes.

Various dispensers and/or purification devices and techniques are disclosed in U.S. Pat. No. 1,771,519, No. 2,697,841, No. 2,783,919 and No. 3,772,193. The above patent 3,772,193 discloses a pool chlorine dispenser including a basket and restrictive fabric covering the basket which are formed from polyethylene or polypropylene. Plastic squeeze bottles including removable dropper tips formed from polyethylene or polypropylene in a variety of colors are well known in the prior art for dispensing drops of medication or other liquid.

SUMMARY OF THE INVENTION

The invention is summarized in an iodine dispenser including a squeezable plastic container having a single opening, a removable dropper tip fitted to the opening, and a removable cap secured over the tip to seal the container; a quantity of solid elemental iodine; and means for retaining the solid elemental iodine within the container for being dispensed in a water solution formed by placing water in the container.

An object of the invention is to form an iodine dispenser suitable for storing and dispensing iodine which is relatively inexpensive and sufficiently small to be carried and used in various applications.

Another object of the invention is to produce an iodine dispenser which can be carried by travellers, hunters, campers, fishermen, military personnel and the like and utilized to store as well as dispense iodine for rendering water potable.

Another object of the invention is to produce an iodine dispenser which can impart iodine to destroy pathogens known to collect on the surfaces of vegetables.

Another object of the invention is to produce an iodine dispenser which can impart iodine to use as a wound sanitizer, by applying a sanitizing concentration of iodine directly to cuts, lacerations, abrasions, etc.

Still another object of the invention is to produce an iodine dispenser which can impart iodine to administer orally to humans to cure or prevent iodine-deficient goiter and other medical problems associated with dietary iodine insufficiency.

It is also an object of the invention to produce an iodine dispenser which can be manufactured in large quantities, stockpiled and stored for indefinite lengths of time for distribution in the event of a disaster.

One advantage of the invention is that a single device and procedure can be employed for providing disinfection of water, disinfection of vegetables, cure and/or prevent iodine-deficiency goiter, sanitize wounds and for providing protection against radioactive iodine accumulation in case of a nuclear catastrophe.

Other objects, advantages and features of the invention will be apparent from the following description of the preferred embodiment, taken in conjunction with the accompanying drawings.

BRIEF DESCRIPTION OF THE DRAWINGS

FIG. 1 is a partially exploded elevational view of a dispenser for use in accordance with the invention.

FIG. 2 is a plan view of an iodine vessel included within the bottle of FIG. 1.

FIG. 3 is a plan view of a modified iodine vessel for inclusion in the bottle of FIG. 1.

FIG. 4 is a plan view of a second modified iodine vessel for inclusion in the bottle of FIG. 1.

FIG. 5 is a plan view of a third modified iodine vessel for inclusion in the bottle of FIG. 1.

FIG. 6 is a plan view of an iodine pellet.

FIG. 7 is an elevational view of a dropper tip, a portion thereof broken away, with a filter insert.

FIG. 8 is an elevational view of a modified dropper tip and cap arrangement for the dispenser in accordance with the invention.

DESCRIPTION OF THE PREFERRED EMBODIMENT

As shown in FIG. 1, an iodine dispenser in accordance with the invention includes a squeezable plastic tube container or bottle indicated generally at 10 which contains a quantity of solid elemental iodine with means, such as a porous vessel 12, for retaining the solid iodine in the bottle. The bottle 10 includes a body portion 14 which has a single opening or nipple 16 to which is fitted a removable dropper tip 18 and cap 24.

In the dropper tip and cap arrangement of FIG. 1, an annular rib 20 is formed around the lower portion of the dropper tip 18 which extends inside of the opening through the nipple 16 for cooperating with an annular lip 22 formed on the inside surface of the nipple 16 to removably secure the dropper tip 18 in the nipple 16. The cap 24 is securable over the nipple 16 by means such as mating female threads on the cap and male threads on the nipple for removably sealing the dropper tip 18 and opening 16 of the bottle.

A modified dropper tip 118 in FIG. 8 has internal threads for being secured on the nipple 16. A cap 124 is provided for snap-fitting on the dropper tip 118.

The solid elemental iodine contained in the vessel 12 may be iodine crystals, iodine flakes, powdered iodine or a pellet of iodine 26, FIG. 6. The pellet 26 can be formed by fusing iodine flakes, crystals or powder fines with heat in and iodine-resistant mold, such as a mold made from Hastalloy or a metal coated with a resistant material such as polytetrafluoroethylene. Upon application of heat to the mold, the iodine melts: it is fused quickly by withdrawing the heat source. The pellet 26 can also be formed from iodine particles secured together with an iodine-compatable chemical adhesive. For example, a silicone dispersion liquid such as Dow Corning Q7-2213 Silicone Dispersion, a dimethylsiloxane elastomer is coated with iodine crystals, flakes, powder, or smaller pellets, and then cured; the pellet or ball formed from the cured agglomerated material releases iodine when placed in water. Other adhesive type chemicals can be used.

The iodine vessel 12 and modified iodine vessels 112, 212 and 312 are illustrated in FIGS. 2, 3, 4 and 5, respectively. The vessel 12 is a section of tubing which is porous or otherwise pervious to water and which is sealed at the ends to enclose the iodine within the vessel. The modified vessel 112 is formed from a screen 114 supported by a frame 116, the frame and screen being plugged or capped at the opposite ends to form a closed container for the iodine. The modified vessel 212 of FIG. 4 is in the form of a capsule having respective telescoping halves 214 and 216 formed from porous material. The modified vessel 312 of FIG. 4 is a bag formed from a cloth or plastic mesh. Various other possible vessels for containing the iodine could possibly be employed. All of the vessels for containing the iodine are porous and pervious to passage of water but have the perforations or openings therein sufficiently small to retain undissolved iodine therein. The vessel is formed from a suitable material which is non-reactive with iodine and water. One of the vessels or pellets containing iodine is placed within each of the body portions 14 or dropper tips 18 or 118 during the assembly of the bottles 10, or at a later date by removing the cap and/or dropper tip and then reassembling each bottle. The iodine containing vessel or pellet can be secured by press fitting, adhesives, etc. in the dropper tip during assembly.

As an alternative to a porous vessel, the means for retaining the solid iodine in the bottle can be formed in the dropper tip 18 or 118. Where an iodine containing pellet is used, the outlet orifice in the dropper tip is sufficiently small to retain the pellet in the bottle. In another arrangement illustrated in FIG. 7 for the dropper tip 18, the means for retaining the iodine in the bottle is a filter 28. The filter 28 is a foam, mesh or grid formed from a material which is compatible with iodine and water. The filter 28 is secured in the dropper tip 18 or 118 such as being press fit or fastened by an adhesive or other means.

The bottle 10 is formed from a plastic material which is also compatible with iodine and water. Suitable materials include thermoplastics such as polyvinyl chloride, high-density polyethylene or polypropylene. Preferably the bottle 10 has a relatively dark color i.e., the bottle is formed from a plastic material which includes a dark pigment. Suitable dark pigments include dark blue pigments, black pigments, and amber brown pigments suitable for inclusion in plastic materials containing medications or food products. It has been found that light colored or white bottles permit iodine migration or loss while dark colored bottles suffer from substantially less iodine migration and loss, except in polyvinyl chloride bottles where no loss has been noted. The reason for substantially greater iodine migration and loss in white or light colored polyethylene or polypropylene bottles compared to iodine migration and loss in dark colored polyethylene or polypropylene bottles or in polyvinyl chloride bottles is not understood.

In use of the iodine dispenser and practice of the present method, water is placed in the bottle 10 whereupon a small amount of the iodine is dissolved in the water. The water can conveniently be placed in the bottle by removing the cap and dropper tip and pouring the water through the opening 16. After replacing the dropper tip, the water solution of iodine is then dispensed by means of the dropper tip for disinfection of water and/or treatment. For disinfection a few drops of the iodine solution from the bottle can be placed in a container of water to render the water potable within a few minutes of time.

Accumulation of radioactive iodine within human and livestock thyroid glands can produce disease states including thyroid cancer. In event of a nuclear disaster, such as an accident at a nuclear power plant or a nuclear attack, radioactive iodine is a primary health concern for survivors. Treatment of human beings and livestock with iodine dispensed by the present dispenser serves to prevent the accumulation of radioactive iodine. The iodine from the dispenser will increase the quantity of iodine within the blood serving to reduce the fraction of any radioactive iodine that is taken up by the thyroid gland since the thyroid gland only accumulates a certain quantity of iodine over a period of time. Suggested dosage for health protection of adults is about 20 mg of iodine daily for the first two or three days, followed by maintenance dosage rates of 5 mg/daily. Dosage rates for children is 1.5 to 2.0 mg/daily. Thus in the event of a nuclear disaster, the present dispenser can be used to dispense iodine into drinking water to simultaneously serve two purposes in safeguarding the public health; namely, (1) the disinfection of water from pathogenic microbes and (2) the prevention of absorption of radioactive iodine.

The disease of iodine-deficiency goiter is considered by the United Nations World Health Organization to afflict over 220 million people throughout the world. The iodine-dispensing device can supply via drinking water the amount of iodine considered necessary to resolve this wide-spread disease and its associated disease stated, i.e., 100 to 200 micrograms of iodine per person daily.

In addition to drinking water as a known vector for disease, another notorious vector is contaminated vegetables. The device can provide heavy iodine concentrations to water wherein vegetables can be placed and sanitized. Pathogenic bacteria, viruses, fungi, protozoöns and their cysts, nematodes and worms will be destroyed, protecting the consumer.

Iodine, in aqueous and alcoholic solutions, has enjoyed official status in the U.S. Pharmocopoeia since 1830 as a remarkable wound disinfectant or sanitizing agent. For nearly a century and one-half, tincture of iodine in alcohol has been a common item in the home medicine cabinet. Complaints of pain due to the use of alcoholic iodine tinctures are also common, whereas experience shows no pain is elicited with aqueous iodine solution of sufficient strength to destroy pathogens. Titrated iodine strengths of 10, 12.5, 25 and 50 milligrams per liter (mg/l) have been used for decades in the United States to sanitize cow udders prior to milking. Iodine concentration in the described dispenser is several times these strengths, and can be applied directly to the wound from the dispenser, effecting wound disinfection.

Elemental iodine is barely soluble in water; for example, water at a temperature of about 22° C. (70° F.) saturates at about 305 milligrams iodine per liter (mg/l) or 305 parts per million. At 30° C. (86° F.), the amount of iodine in water at saturation is about 400 mg/l. At 10° C. (50° F.), iodine in water at saturation is approximately 225 mg/l. When iodine is placed in water, the hydrolysis of iodine ($I_2$) is: $I_2 + H_2O = HIO + H^+ + I^-$. However, in the concentration present in saturation, the iodine products will be iodine ($I_2$), hypoiodous acid (HOI), dissociated iodide ion ($I^-$), and hypoiodite ion ($IO^-$), with $I_2$ and HOI vastly predominating. Triiodide (polyiodide) is the other specie present, formed by the reaction of $I_2 + I^-$. These are reversible reactions and when concentrated iodine solution is added to water not containing iodine, only $I_2$ and HOI are formed heavily, at disinfection levels. The relationship of specie predominance is dictated by pH. Adding iodine to establish a final active residual of 0.5 mg/l in water at a pH of 5 produces 99% $I_2$ and 1% HOI. At pH 7, $I_2$ is 52%; HOI, 48%. At pH 8, $I_2$ is 12%; HOI 88%, with a trace of hypoiodite ion (less than 0.005%). At pH 8, there are 22,000 undissociated HOI molecules to one hypoiodite ion.

Since only a small quantity of iodine is dissolved in water, ample iodine can be included within the vessel enabling the device to be reused when devoid of water; i.e., the bottle 10 can be refilled with water to form additional iodine solution. Additionally, the iodine vessel containing iodine can be easily replaced within the bottle upon exhaustion. Stockpiling of iodine capsules for insertion into the original bottle would be easy and not space consuming.

The present dispenser can be manufactured and stockpiled in large quantities. The dispenser, particularly when the plastic squeeze bottle is a dark color, has a relatively long or indefinite storage life. Plastic covers, such as shrink fitted polyvinylidene chloride covers, can be placed on the dispensers to further insure long storage life.

Since the present invention is subject to many modifications, variations and changes in detail, it is intended that all matter in the foregoing description or shown in the accompanying drawing be interpreted as illustrative and not in a limiting sense.

What is claimed is:

1. A method of storing and dispensing iodine comprising placing a quantity of solid elemental iodine in a removable dropper tip, securing the quantity of solid elemental iodine in the dropper tip during the placing of the iodine in the dropper tip, fitting the removable dropper tip to the single opening of a squeezable plastic container, securing a cap over the dropper tip whereby the iodine is sealed in the container for storage, opening the container by removing the cap and dropper tip, inserting a quantity of water in the container through the single opening, replacing the dropper tip, squeezing the container to dispense a water solution of iodine, and retaining undissolved elemental iodine in the container.

2. A method as claimed in claim 1 wherein the squeezable plastic container is formed from polyvinyl chloride, dark colored polyethylene, or dark colored polypropylene.

3. A method as claimed in claim 1 wherein the container is a dark color, and the container is formed from polyethylene or polypropylene.

4. A method as claimed in claim 1 wherein the water solution of iodine is dispensed into a larger quantity of water for destroying pathogens in the larger body of water.

5. A method as claimed in claim 1 wherein the water solution of iodine is administered orally to a mammal to prevent accumulation of radioactive iodine in a thyroid gland.

6. A method as claimed in claim 1 wherein the water solution of iodine is administered orally to a human being at a dosage in the range from about 1.5 mg to 20 mg iodine daily to prevent accumulation of radioactive iodine in a thyroid gland.

7. A method as claimed in claim 1 wherein the water solution of iodine is administered to a mammal by adding the water solution to a quantity of drinking water to disinfect the drinking water.

8. A method as claimed in claim 1 wherein the water solution of iodine is administered to mammals by adding the water solution to a quantity of drinking water to provide dietary iodine sufficiency in areas of dietary iodine insufficiency that has resulted in iodine-deficiency diseases.

9. A method as claimed in claim 1 wherein the water solution of iodine is administered directly to wounds for sanitization of wound sites.

10. A method as claimed in claim 1 wherein the water solution of iodine is used to disinfect vegetables.

* * * * *